United States Patent
Kohlert et al.

(10) Patent No.: US 9,201,007 B2
(45) Date of Patent: Dec. 1, 2015

(54) DEVICE FOR DETERMINATION OF GAS CONCENTRATION

(71) Applicant: Infineon Technologies AG, Neubiberg (DE)

(72) Inventors: Dieter Kohlert, Pentling (DE); Gerhard Poeppel, Regensburg (DE); Franz Schreier, Planegg (DE)

(73) Assignee: Infineon Technologies AG, Neubiberg (DE)

( * ) Notice: Subject to any disclaimer, the term of this patent is extended or adjusted under 35 U.S.C. 154(b) by 169 days.

(21) Appl. No.: 13/851,879

(22) Filed: Mar. 27, 2013

(65) Prior Publication Data
US 2013/0258315 A1    Oct. 3, 2013

(30) Foreign Application Priority Data
Mar. 27, 2012 (DE) .................. 10 2012 006 047

(51) Int. Cl.
| | |
|---|---|
| *G01J 3/00* | (2006.01) |
| *G01N 21/61* | (2006.01) |
| *G01N 21/3504* | (2014.01) |
| *G01N 21/35* | (2014.01) |

(52) U.S. Cl.
CPC ............ *G01N 21/61* (2013.01); *G01N 21/3504* (2013.01); *G01N 2021/3513* (2013.01); *G01N 2021/3595* (2013.01); *G01N 2201/0636* (2013.01)

(58) Field of Classification Search
CPC .............. G01J 3/02; G01J 3/42; G01N 21/31; G01N 21/552
USPC ........................................ 356/300
See application file for complete search history.

(56) References Cited

U.S. PATENT DOCUMENTS

| | | | |
|---|---|---|---|
| 3,723,007 A | | 3/1973 | Leonard |
| 4,410,271 A | * | 10/1983 | Matthews .................. 356/301 |

(Continued)

FOREIGN PATENT DOCUMENTS

| | | |
|---|---|---|
| DE | 10 2008 001 440 A1 | 7/2009 |
| EP | 0 235 404 A2 | 9/1987 |
| EP | 2 503 323 A2 | 9/2012 |

OTHER PUBLICATIONS

Huang, S., et al., "Spatial and Temporal Distributions of a Gaseous Pollutant During Simulated Preventive Maintenance and Pipe Leaking Events in a Working Cleanroom," IEEE Transactions on Semiconductor Manufacturing , Aug. 2009, pp. 391-398, vol. 22, No. 3.

*Primary Examiner* — Tarifur Chowdhury
*Assistant Examiner* — Md Rahman
(74) *Attorney, Agent, or Firm* — Slater & Matsil, L.L.P.

(57) ABSTRACT

A device can be used for establishing gas concentrations in an examination volume. A radiation source is configured to generate an electromagnetic beam. A beam guiding apparatus is arranged downstream of the radiation source. The beam guiding apparatus is configured to set a plurality of variations of beam guidance of the beam entering the beam guiding apparatus in an observation plane in the examination volume. A spectrometer is arranged downstream of the beam guiding apparatus. The spectrometer is configured to carry out a spectral analysis of the beam leaving the beam guiding apparatus. An evaluation unit is configured to establish in the observation plane a 2D concentration distribution for one or more gases in the examination volume on the basis of the spectral analysis for different variations of beam guidance.

28 Claims, 6 Drawing Sheets

(56) References Cited

U.S. PATENT DOCUMENTS

| | | | |
|---|---|---|---|
| 6,341,521 B1* | 1/2002 | Bartolomey et al. | 73/31.03 |
| 7,372,573 B2* | 5/2008 | Spartz et al. | 356/451 |
| 8,462,347 B2* | 6/2013 | Phillips et al. | 356/451 |
| 2006/0203248 A1 | 9/2006 | Reichardt et al. | |
| 2006/0238768 A1* | 10/2006 | Brorson et al. | 356/451 |
| 2009/0027654 A1* | 1/2009 | Takahashi et al. | 356/36 |
| 2009/0229344 A1* | 9/2009 | Nakaso | 73/24.01 |
| 2011/0096800 A1* | 4/2011 | Weida et al. | 372/20 |
| 2011/0112772 A1* | 5/2011 | Yost et al. | 702/24 |

\* cited by examiner

DEVICE FOR DETERMINATION OF GAS CONCENTRATION

This application claims priority to German Patent Application 102012006047.5, which was filed Mar. 27, 2012 and is incorporated herein by reference.

TECHNICAL FIELD

Embodiments of the present invention relate to a device for determination of gas concentration.

BACKGROUND

Chemical trace gas analysis in cleanrooms is a necessity in order to identify possible contaminations in good time and to detect the sources thereof. Until now, a number of methods have been used in cleanrooms (e.g., in semiconductor manufacturing) for the trace gas analysis.

In a first example, collection vessels are put up and, after a certain time of exposure in the cleanroom, the built-up concentration is evaluated by chemical/physical analysis, for example, by means of atomic absorption spectroscopy (AAS), gas chromatography (GC), inductively coupled plasma mass spectrometry (ICP-MS).

In a second example, use is made of individually put-up gas sensors and the corresponding signals thereof are evaluated. Such a method is known, e.g., from the article "Spatial and Temporal Distributions of a Gaseous Pollutant During Simulated Preventive Maintenance and Piping Leaking Events in a Working Cleanroom" by Shih-Hsuan Huang, et al., IEEE Transactions on Semiconductor Manufacturing, volume 22, number 3, August 2009. Here, mobile FTIR spectrometers (FTIR="Fourier transform infrared spectrometer" or "Fourier transformation infrared spectrometer") are used in the cleanroom for the gas measurement.

It is disadvantageous that the first method does not permit a fine resolution in time, since the concentration is built up integrated over time. Furthermore, the possible spatial resolution is restricted in the first example because the network of assembly points cannot be selected to be arbitrarily dense or because some points in the cleanroom are simply inaccessible, for example, the space above a manufacturing plant. This restriction largely also applies to the individually put-up gas sensors in the second example. Further disadvantages include cross contaminations, which are caused by handling the analytic instruments themselves during both the mentioned examples.

SUMMARY OF THE INVENTION

In one aspect, the invention specifies a device for establishing (trace) gas concentrations in an examination volume, in particular in a cleanroom, which device overcomes the aforementioned disadvantages and provides a spatially and temporally resolved analysis of even a plurality of gases even in the case of very low gas concentrations.

A device can be used for establishing (trace) gas concentrations in an examination volume, for example, in a cleanroom. The device according to the invention comprises a radiation source, by means of which an electromagnetic beam can be generated, a beam guiding apparatus which is arranged downstream of the radiation source and by means of which a multiplicity of variations of beam guidance of the beam entering the beam guiding apparatus can be set in an observation plane in the examination volume, a spectrometer which is arranged downstream of the beam guiding apparatus and by means of which it is possible to carry out a spectral analysis of the beam leaving the beam guiding apparatus, a control unit for controlling the radiation source, the beam guiding apparatus and the spectrometer, and an evaluation unit, by means of which it is possible to establish in the observation plane a concentration distribution for one or more gases in the examination volume on the basis of the spectral analysis for the different variations of beam guidance.

BRIEF DESCRIPTION OF THE DRAWINGS

FIGS. 11 and 12 show a schematic diagram of a measurement geometry for two-dimensional scanning of the cleanroom by synchronous, parallel movement of the mirror pair M1 and M2 in the y-direction and/or M4 and M5 in the x-direction. The circles denote a region of locally increased gas concentration in the cleanroom;

FIG. 13 shows a scanning pattern, in which the increment of the mirror-pair movements is tuned after registering increased concentrations (denoted by the concentric rings). In the present case, FIG. 13 is based on the measurement geometry of FIGS. 11 and 12;

DETAILED DESCRIPTION OF ILLUSTRATIVE EMBODIMENTS

Embodiments of the invention relates to a device for establishing (trace) gas concentrations in an examination volume, in particular in a cleanroom. Here, a cleanroom or ultra-cleanroom is understood to mean a room in which the concentration of airborne particles is kept as low as necessary. Here, the two terms (cleanroom and ultra-cleanroom) are used synonymously. Cleanrooms are required for special manufacturing processes, particularly in semiconductor manufacturing where particles present in normal surrounding air would interfere with the structuring of integrated circuits in the range of fractions of a micrometer. Further applications of cleanrooms or cleanroom technology are found in optics and laser technology, aerospace engineering, the life sciences and in medical research and treatment, the research and germ-free production of foodstuffs and medication and in nanotechnology.

The present invention is, in particular embodiments, based on trace gas analytical measurements by means of spectroscopy, for example, infrared spectroscopy or differential optical absorption spectroscopy (DOAS), which has already proven its worth in trace gas analysis in the atmosphere. Here, as a result of skillful guidance of the light paths, it is now possible to achieve high resolutions in both time and space (time: second to minute range; space: cm range). At the same time, this optical method is suitable for resolving even very small (ppb-ppm) gas concentrations.

In the following text, the device according to the invention is substantially described using the example of measuring the gas concentration in a cleanroom, without this restricting the general inventive concept.

Since various gas components can be "measured" simultaneously using the device according to the invention, this can be referred to as a multivariate, temporally and spatially resolved gas analysis. Points in a cleanroom which are particularly sensitive or of particular interest can be observed in a targeted fashion by appropriate variations of path guidance of the beam ST, generated by the beam source Qu, to the spectrometer S, for example, as a result of multiple reflections on minors or with the aid of optical waveguides.

Transmission measurements (absorption spectroscopy) are preferably carried out at short time intervals in the present device. For the measurement, use is preferably made of known infrared radiation measurement methods, such as Fourier transform infrared spectroscopy (FTIR), differential optical absorption spectroscopy (DOAS), thermography, laser spectrometry or the like. Alternatively, or in addition thereto, it is possible to capture the microwave or ultraviolet radiation properties of the gases in the cleanroom. In the following text, the device according to the invention will be described for (FT)-IR; the transfer to other methods occurs analogously.

In an absorption measurement arrangement, broadband radiation sources in the infrared and microwave spectral range (or optionally in the visible and ultraviolet spectral range) are used, for example, black-body emitters (black bodies), Globar emitters, Ecosorb, etc., which are tuned to the radiation-active spectral ranges of the gases of interest. However, in the case of appropriate specific problems, it is also possible to use narrowband radiation sources such as lasers or laser diodes.

In accordance with the radiation transport theory in homogeneous gaseous media, the radiation absorbed along a path L is, according to the Beer-Lambert law, described by:

$$\mathcal{T}(v) = \frac{I(v)}{I_0(v)} \quad (1)$$

$$= \exp\left(-L\sum_g k_g(v, p, \mathcal{T})\rho_g\right) = \prod_g \mathcal{T}_g(v) \quad (2)$$

Here, $\tau$ is the transmission as a function of the wavenumber $v$ (or wavelength $\lambda \sim 1/v$) which is defined as the ratio of the radiation intensity $I(v)$ measured by the observer/instrument to the radiation $I_0(v)$ emitted by the radiation source. In the case of a black-body emitter at a temperature T, this is specified by the Planck function $B(v, T)$. In order to take into account the effects of instruments, this should be convolved in a technically known fashion with a suitable instrument line-profile function.

The sum in (2) extends over all gases (molecules) g, absorbing in the observed spectral range, with the density (concentration) $\rho_g$ and the absorption cross section $k_g$, which depends on pressure and temperature. In the case of high-resolution infrared spectroscopy, this can be calculated with the aid of a so-called line-by-line model by summing the contributions of all relevant spectral lines (rotation and rotation/vibration transitions), $$k(v, p, T) = \sum_l S_l(T) f(v_i \hat{v}_l, \gamma_l(p, T)) \quad (3)$$

$$= \sum_l S_l(T) \frac{\gamma_l/\pi}{(v - \hat{v}_l)^2 + \gamma_l^2} \quad (4)$$

Here, each spectral line is described by its line position $\hat{v}_l$, the (temperature-dependent) line intensity $S_l$ and the line width $\gamma_l$. In the case of pressure and temperature conditions that can be found in laboratories or cleanrooms (lower troposphere with $p \approx 1$ bar and $T \approx 280 \ldots 290K$), the line broadening is determined by collision processes (pressure broadening with $\gamma_l \sim \rho$; negligible Doppler broadening) and the line profile function f is described by a Lorentzian function. In the case of the aforementioned pressures and temperatures, the line width is in the region $\gamma 0.1$ cm$^{-1}$.

Information in respect of the line parameters position, intensity, width etc. for a multiplicity of gases can be obtained from molecule-spectroscopic databases such as HITRAN or GEISA. For large and complex molecules in particular, for example, CFCs, with a multiplicity of spectral lines, it is impractical or impossible to store the line parameters; in these cases, use should be made of databases containing absorption cross sections.

In accordance with equation (2), it is possible to deduce the gas concentration $\rho_g$ if the transmission $\tau$ is known. When evaluating the measurement, it should be noted that the spectrum (in this case the transmission $\tau$) measured by the spectrometer S does not form a continuous function of the wavenumber, but is only provided at a set of m discrete (not necessarily equidistant) nodes, which form the so-called measurement vector of length m:

$$y_{obs} \equiv \tau_{obs} = (\tau_{obs}(\nu_1), \tau_{obs}(\nu_2), \ldots, \tau_{obs}(\nu_m)). \quad (5)$$

The number n of gases to be detected and the concentrations thereof to be determined $x_g \equiv \rho_g$, $g=1 \ldots n$ is generally significantly smaller than the number of measurement points m. Moreover, the measurement is generally afflicted by noise, and so exact equality is not to be expected and the evaluation is formulated as a "least squares" problem:

$$\min_x \|y_{obs} - y_{mod}(x)\|^2 = \quad (6)$$

$$\min_\rho \sum_{i=1}^m \left[\mathcal{T}_{obs}(\nu_i) - \exp\left(-L \sum_g k_g(\nu, p, T)\rho_g\right)\right]^2$$

If the absorption of all gases in the observed spectral range is small, i.e., if $\tau \approx 1$, the nonlinear least squares problem (5) can be transformed into a linear least squares problem by a Taylor expansion in the transmission. If only the absorption of the gases X, Y to be determined is small, i.e., $\tau_X \approx 1$, $\tau_Y \approx 1$ but $\tau_{remainder} < 1$, this can likewise be transformed into a linear least squares problem by a corresponding expansion. In the "mixed case," i.e., $\tau_X \approx 1$, $\tau_Y < 1$ (gas X weakly absorbing/gas Y strongly absorbing), the least squares problem can be solved with the aid of the "variable projection" method, which is known to a person skilled in the art.

For simultaneous measurement of a plurality of gases, a broadband capture of large spectral ranges with a high spectral resolution is advantageous. In this respect, Michelson-type Fourier spectrometers with detectors tuned to the selected spectral ranges are particularly suitable; however, it is also possible to make use of other types such as, e.g., grating spectrometers, provided that these satisfy the requirements in respect of resolution and signal-to-noise ratio. The required resolution of the spectrometer S should, in general, correspond to the natural line width γ of the gases to be observed, i.e., of the order of $\delta\nu \approx 0.1$ cm$^{-1}$ in the aforementioned pressure and temperature conditions. In the case of measurements in closed absorption cells with a reduced pressure (cf. below), the spectrometer S should accordingly also render possible measurements with correspondingly higher resolution (smaller $\delta\nu$ as a result of $\gamma \sim p$).

Figure 1:
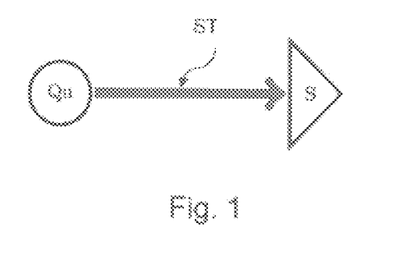
FIG. 1 shows a basic measurement geometry with radiation source Qu and spectrometer S and a simple direct radiation path.

In the case of the simplest absorption measurement arrangement, the gas mixture to be examined is situated in an examination volume between the radiation source Qu and the spectrometer S, through which the beam ST emerging from the radiation source Qu passes. See FIG. 1 in this respect, wherein, in the process, some of the energy of the beam ST is absorbed in a wavelength-specific manner, in accordance with the composition of the gas. In one embodiment of the beam guiding apparatus LE, the optical path can be extended by one or more minors M, and so this is captured depending on the arrangement of the minors M in the cleanroom, see FIG. 2 in this case.

Figure 2:
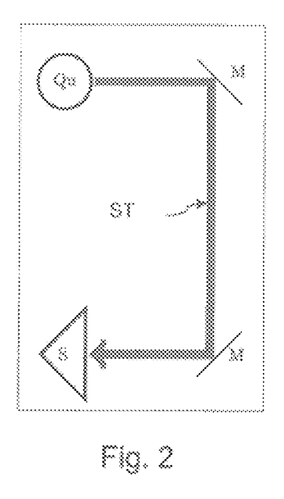
FIG. 2 shows a schematic diagram of a measurement geometry with a long path through the cleanroom from the radiation source Qu to the spectrometer S via two mirrors M.
Figure 3:
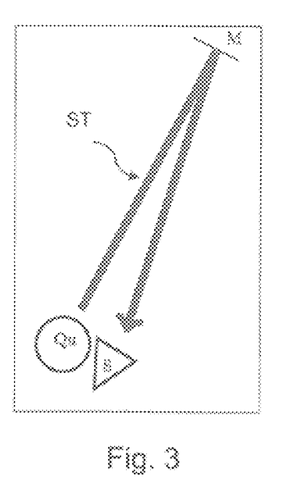
FIG. 3 shows a schematic diagram of a measurement geometry with combined radiation source Qu and spectrometer S, and mirror or retroreflector M.

In FIG. 2, the beam guiding apparatus LE comprises two mirrors M. In FIG. 2 and the following figures, the cleanroom is respectively indicated as a rectangular frame, which surrounds the radiation source Qu, the spectrometer S, mirrors M and the entire radiation path. An alternative embodiment with the source Qu and spectrometer S placed together (or tightly adjacent to one another) is shown in FIG. 3. As a result of the robustness thereof and the simpler adjustment, in this case a retroreflector can also be used in place of the mirror M. In this case, the beam guiding apparatus LE comprises one minor M.

Figure 4:
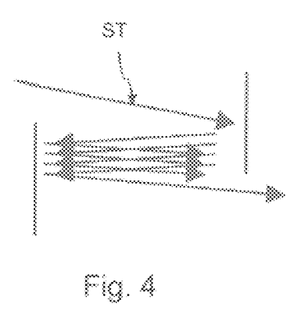
FIG. 4 shows a schematic diagram of a beam path in a multi-reflection cell.

However, for a targeted spatial capture of the gas concentrations, a short measurement path (between source Qu and spectrometer S) is more advantageous at the point to be examined. As a result of the low concentrations of the gases in normal conditions (for example, in the surrounding air), the "geometric path" usually does not suffice for significant absorption signatures. In a preferred variant, the beam guiding apparatus LE therefore comprises a multi-reflection cell (open or closed absorption cell, White cell, cf. FIG. 4); in the case of laser spectroscopy, use can also be made of a Herriott cell, which enables optical paths up to several hundred meters. In this case, the path length L in equation (2) should be identified with the overall optical path length, i.e., a multiple of the mirror spacing.

Figure 5:
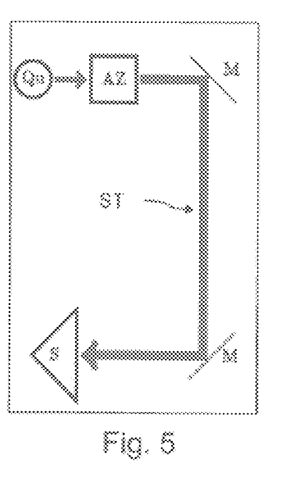
FIG. 5 shows a schematic diagram of a measurement geometry with a radiation source Qu, an absorption cell AZ or White cell, and a spectrometer S arranged separately from Qu.

Commercially available compact and robust multi-reflection cells with dimensions of the order of a few decimeters and optical path lengths up to approximately 10 m enable a spatially targeted measurement at the critical points in the cleanroom, which, as a result of the small cell volume (of the order of up to a few liters) and the efficient and fast gas exchange connected therewith, allows measurements at short temporal intervals. In accordance with the beam guidance sketched in FIG. 5, the beam ST emitted by the radiation source Qu is guided to the spectrometer S from the absorption cell AZ (multi-reflection cell) by means of one or more minors M or alternatively by optical waveguides. The beam guiding apparatus LE therefore comprises the absorption cell AZ (multi-reflection cell) and the mirrors M or, alternatively or additionally, optical waveguides.

Figure 6:
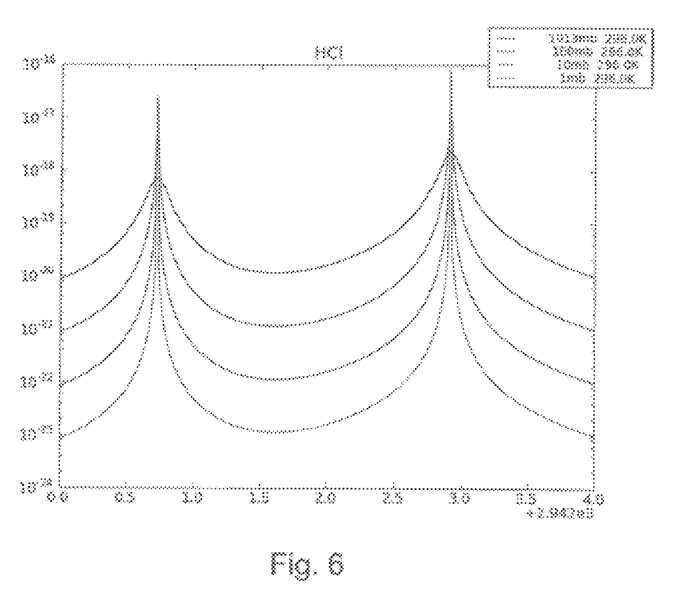
FIG. 6 shows HCl effective cross sections for various pressures.

Identifying and quantitatively evaluating the transmission spectra for deriving the concentration of the relevant gases is often made more difficult by virtue of the fact that the absorption lines thereof are generally superposed by the absorption lines of a multiplicity of further gases present in the air and are possibly covered, in particular by water in almost the whole infrared microwave spectral range and, depending on the selected spectral range, by further "interfering" gases, e.g., carbon dioxide $CO_2$, ozone $O_3$, methane $CH_4$, etc. In accordance with equation (3), the height of the peak of a spectral line (or the depth of a line in the transmission spectrum as a result of equation (2)) is determined by the full width at half maximum γ in addition to the line intensity S. For an individual line in the line center, $k \sim S/\gamma$ applies for the effective cross section for $\nu \approx \hat{\nu}$; by contrast $k \sim S\gamma/(\nu-\hat{\nu})^2$ applies in the line wing for $\nu-\hat{\nu} \gg 0$. Thus, a spectral line is ever more pronounced and therefore easier to measure the smaller the full width at half maximum is; in this respect, cf. FIG. 6 in which exemplary HCl effective cross sections are illustrated for various pressures. Accordingly, the "base contribution" of the interfering species reduces with reducing line width. Since the line width is proportional to the surrounding pressure, use is preferably made of an alternative measuring arrangement in a closed cell (optionally a multi-reflection cell) with reduced pressure.

Most of the gases of interest for the chemical trace analysis in laboratories, more particularly in cleanrooms, are present only in extremely low concentrations (ppb to ppt) in the natural surrounding air (lower troposphere). In general, all relevant gases have transitions in the infrared and microwave spectral range. Since, in accordance with equation (2), the transmission τ constitutes a superposition of the transmission of the individual gases $\tau_g$, spectral ranges in which the absorption of gas X is significant but the absorption of all other gases relevant in the observed spectral range is small, i.e., where $\tau_X < 1$ and $\Pi_{g \neq X} \tau_g \approx 1$, are particularly suitable for determining the concentration of the gas X.

The suitable spectral ranges for various gases relevant in cleanrooms are known from the literature or can be gathered from the databases (e.g., HITRAN or GEISA). In addition to the absorption bands, the following summary shows particularly suitable spectral ranges of some gases of interest:

$HNO_3$ Nitric acid: Atmospheric background concentration pursuant to "U.S. standard": $5*10^{-5}$ ppm, MAK (occupational exposure limit)=5 $mg/m^3$=2 ppm; several absorption bands in FIR and TIR (far and thermal IR); measurement preferably at $v=458$ $cm^{-1}$ HF Hydrogen fluoride: U.S. standard: $10^{-8}$ ppm, MAK=0.8 $mg/m^3$ 1 ppm; absorption bands: FIR: $41 < \hat{v} < 625$ $cm^{-1}$; TIR: $3269 < \hat{v} < 4370$ $cm^{-1}$; NIR: $7000 < \hat{v} < 7995$ $cm^{-1}$; measurement preferably at $v=4038-4039$ $cm^{-1}$ HCl Hydrogen chloride: U.S. standard: $10^{-3}$ ppm, MAK=3 $mg/m^3 \approx 2$ ppm; absorption bands: FIR: $20 < \hat{v} < 438$ $cm^{-1}$; TIR: $2398 < \hat{v} < 3160$ $cm^{-1}$; NIR: $5169 < \hat{v} < 5830$ $cm^{-1}$ and $7895 < \hat{v} < 8455$ $cm^{-1}$; measurement preferably in the FIR at $v=41.7$ $cm^{-1}$ or in the TIR at $v=2923-2926$ $cm^{-1}$ or $v=2942-2946$ $cm^{-1}$ HBr Hydrogen bromide: U.S. standard: $2*10^{-6}$ ppm, MAK=17 $mg/m^3 \approx 5$ ppm; absorption bands: FIR: $16 < \hat{v} < 397$ $cm^{-1}$; TIR: $2123 < \hat{v} < 2791$ $cm^{-1}$; NIR: $4593 < \hat{v} < 5164$ $cm^{-1}$ and $7048 < \hat{v} < 7496$ $cm^{-1}$ and $9332 < \hat{v} < 9759$ $cm^{-1}$; measurement preferably at $v=100$ $cm^{-1}$ $H_2O$ Water: There are a number of absorption bands in FIR and TIR. Water absorbs in almost the whole microwave and infrared spectral range, in particular also in the spectral ranges relevant for the other gases of interest. The water vapor concentration can therefore be simultaneously also determined in all cases.

These aforementioned spectral ranges are particularly suitable for detection in the case of low concentrations. In the case of higher concentrations, other spectral regions with weaker lines of the relevant gases may be more suitable since saturation of the lines should be avoided. In particular, in contrast to other methods, there is no upper limit for the detectability of a gas as a result of the option of using suitable spectral ranges during the evaluation depending on the concentration (which spectral ranges are all measured in the case of a spectrometer, such as FT, operating on broadband principles).

The main aim of the invention is the spatially resolved and real-time capture of the gas concentrations, in particular of local "contaminations" as a result of leaks, etc. For scanning of the whole cleanroom which is as automated as possible, it is therefore expedient to "multiply" the configurations shown in FIGS. 2, 3 and 5 such that "scanning" of the cleanroom can take place with a predetermined spatial and temporal resolution.

FIG. 7 to FIG. 10 show further embodiments of the device, in which the source QU/spectrometer S is housed in a common housing, wherein an incident beam ST is directed into the spectrometer S by means of, for example, a beam splitter.

Figure 7:
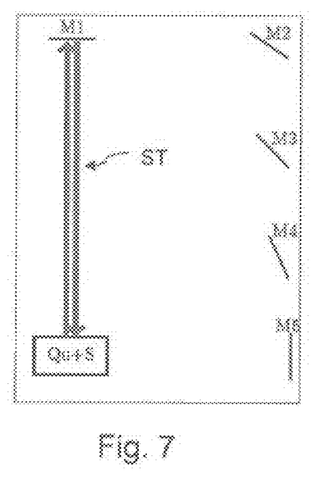
FIGS. 7 and 8 show a schematic diagram of a measurement geometry with combined radiation source Qu and spectrometer S and also a plurality of mirrors (or retroreflectors) (M1, M2, . . . ) which can be "driven at" sequentially. If need be (low absorber concentrations), this measurement design can be extended by a multi-reflection optical unit. In the present case, the radiation source Qu and the spectrometer S are connected by a corresponding mechanical/optical coupling in such a way that a common viewing direction is ensured.
Figure 8:
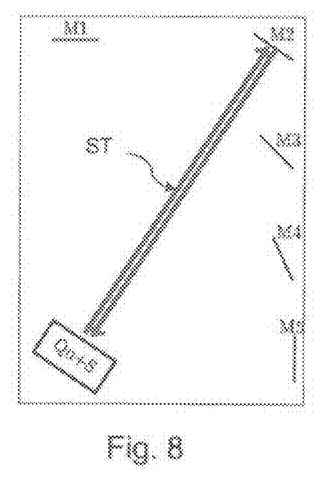

In FIG. 7 and FIG. 8, the spatial scanning of the whole cleanroom is made possible by the sequential and repeated actuation of various mirrors M1, M2, . . . (or retroreflectors) distributed in the room, wherein the various mirrors are "illuminated" in accordance with the beam direction of the beam ST leaving the radiation source Qu. The observed spatial area emerges from the "viewing angle" of the source/spectrometer. In this case, the beam guiding apparatus LE comprises the mirrors M1, M2, . . . and an apparatus for influencing the beam direction of the beam ST leaving the beam source. Since, according to equation (2), the absorption depth of a spectral line increases with the path length L, it is possible, in the case of a unique assignment of viewing angles and path lengths to the various minors, to deduce the path length Qu/S→M from the depth of the spectral line of a gas with the known concentration (e.g., carbon dioxide with approximately 380 ppm) and an additional, independent check of the current measurement geometry is obtained thereby.

Figure 9:
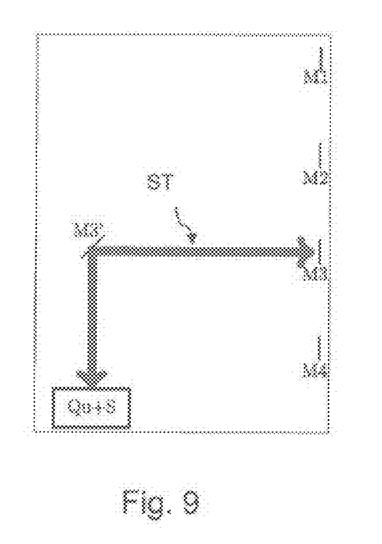
FIGS. 9 and 10 show a schematic diagram of a measurement geometry with combined radiation source Qu and spectrometer S and also a plurality of mirrors (or retroreflectors) (M1, M2, . . . ). The various mirrors (M1, M2, . . . ) are actuated by "folding/unfolding" of the auxiliary mirrors (M1', M2', . . . )
Figure 10:
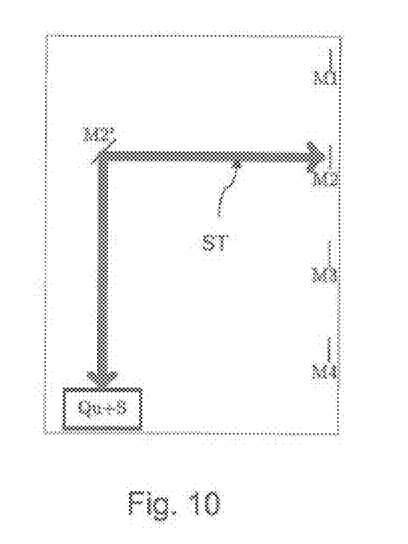

FIG. 9 and FIG. 10 show an alternative arrangement, in which all mirrors M1, M2, . . . are mounted in a row on one wall of the cleanroom. An associated auxiliary mirror M1', M2', . . . , which is arranged on the opposite wall of the cleanroom, corresponds to each minor M1, M2, . . . , and said auxiliary mirrors are folded open and shut in sequence such that the whole room can successively be captured (virtually one-dimensionally by the respective measurement path between the minors Mi and Mi' with i=1 to n). In the present case, the beam source Qu and the spectrometer S are fixed in the observation plane. In FIG. 9, the auxiliary minor M3' in FIG. 10 is folded in front of the auxiliary mirror M2'. However, since only a finite number of minor pairs (with a spacing of decimeters to meters) can be realized in a sensible manner, the spatial resolution is accordingly restricted and local increases in concentration cannot be captured therewith in certain circumstances (this analogously also applies to FIG. 7 and FIG. 8).

Instead of a restricted number of mirror pairs, it is therefore advantageous to use a movable mirror pair which can be freely displaced in the whole cleanroom (i.e., two mirrors M and M' which can be moved synchronously in the y-direction or in the x-direction, for example, by means of synchronously controlled stepper motors or threaded rods). In the case of an appropriate control, the whole room can therefore be captured incrementally in the "normal mode"; if a locally increased gas concentration is detected, the corresponding region of the room can be scanned more finely, i.e., the increments can be reduced.

In a particularly preferred embodiment, the beam guiding unit LE comprises, for example, a minor pair M1 and M2 which can be displaced in the y-direction, and, arranged perpendicular thereto, a minor pair M4 and M5 which can be displaced in the x-direction.

Figures 11, 12, 13:
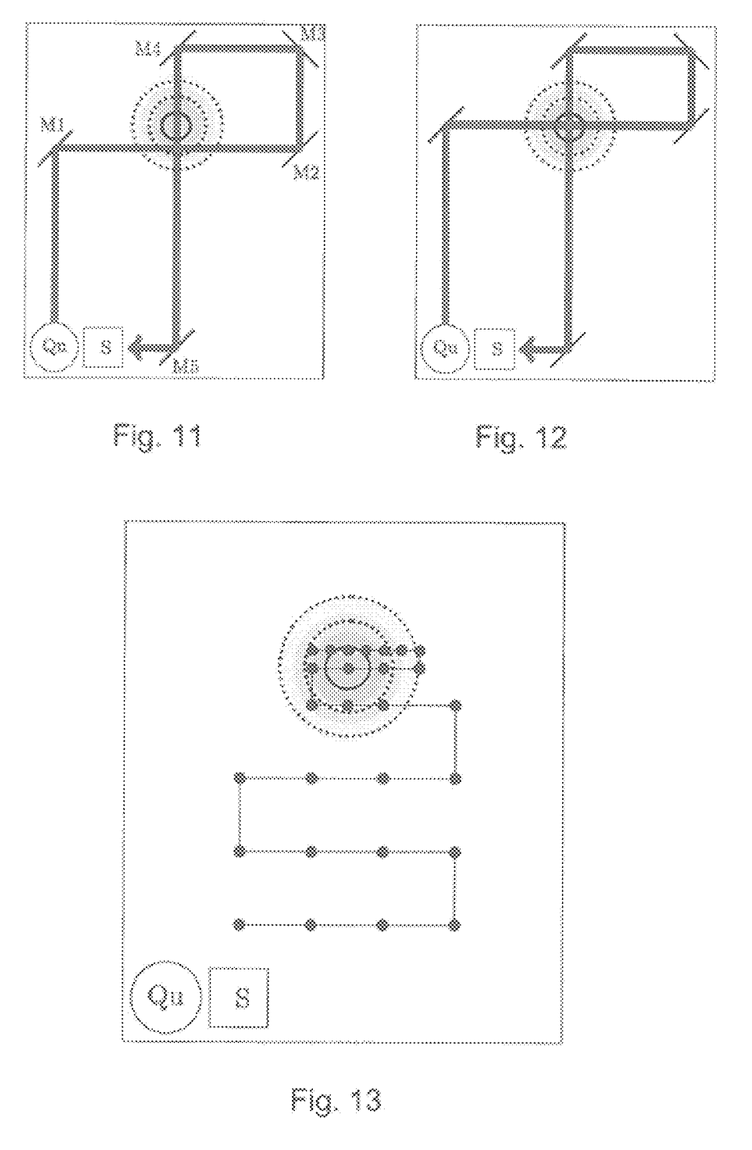

A device with such a beam guiding unit LE for simultaneously capturing the two spatial directions x/y is sketched in FIG. 11 and FIG. 12 (a variant is sketched in FIG. 17), wherein use is made of two minor pairs M1/M2 and M4/M5 which can be moved synchronously. As a result of the common displacement of the two mirrors M1/M2 in the y-direction and the common displacement of the mirrors M4/M5 in the x-direction, it is possible to scan the whole cleanroom in one observation plane. The movement of the two minor pairs M1/M2 and M4/M5 preferably occurs independently of one another and preferably occurs incrementally. A movement of the minor pairs in such a way that the point of intersection of the light paths between M1-M2 and M4-M5 scans the space in "zigzag"-type manner, or similar, is advantageous, as illustrated in FIG. 13. The increment of the scan can in this case be adapted to the currently measured concentrations. Here, the concentric circles in FIGS. 11-13 and 17 specify an exemplary concentration distribution in the cleanroom.

In contrast to the devices sketched in FIGS. 7 to 10, the path length of the light beam is identical for all positions of the mirror pairs M1/M2 and M4/M5 in FIGS. 11 and 12. In the case of uniform gas distributions (the concentrations of all examined gases are constant in the whole observed cleanroom) the measured spectrum therefore is independent of the minor positions. Changes in the spectrum are an indication of changes in concentration. If the concentration of a gas increases, the transmission spectrum is modified in the region of the absorption bands of this gas, if the light beam captures the region with increased concentrations. For the purposes of modeling the transmission in the case of spatially variable gas concentrations, the exponent in the Lambert-Beer law in equation (2) should be calculated by an integral along the light path:

$$\mathcal{T}(\nu) = \exp\left(-L\sum_{g \neq X} k_g(\nu, p, T)\rho_g\right) \times \exp\left(-\int_{Path} k_X(\nu, p, T)\rho_X(s)\,ds\right) \quad (7)$$

$$= \exp\left(-\sum_{g \neq X} \tau_g\right) \times \exp(-\tau_X) \quad (8)$$

$$= \mathcal{T}_{remainder} \times \mathcal{T}_X \text{ where } L = \int_{Path} ds = \int_{Qu}^{S} ds \quad (9)$$

where τ denotes the so-called optical depth and, for simplicity, the assumption is made that the concentration of only one gas X is spatially variable and the concentration of all other gases is constant. Moreover, the assumption is made in the following text that homogeneous pressure and temperature conditions prevail in the cleanroom, and the pressure and temperature dependence of the absorption cross sections k(ν, p, T) is no longer specified in the further text. Under the assumption of perfect mirrors with a degree of reflection of r=1.0, only the distance along the light path is relevant for calculating the transmission and the following applies for the optical depth of the gas X:

$$\tau_X = \int_{Qu}^{M1} k_X(\nu)\rho_X(y)\,dy + \int_{M1}^{M2} k_X(\nu)\rho_X(x)\,dx + \quad (10)$$
$$\int_{M2}^{M3} k_X(\nu)\rho_X(y)\,dy + \int_{M3}^{M4} k_X(\nu)\rho_X(x)\,dx +$$
$$\int_{M4}^{M5} k_X(\nu)\rho_X(y)\,dy + \int_{M5}^{S} k_X(\nu)\rho_X(x)\,dx$$

$$= \int_{Qu}^{S} k_X(\nu)\rho_X(s)\,ds \quad (11)$$

Figure 14:
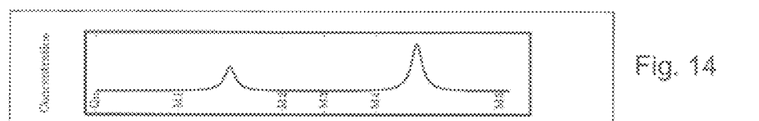
FIG. 14 shows the concentration of a gas, illustrated in a graph, with a local increase as a function of the distance from the radiation source Qu to the spectrometer S along the overall beam path. The illustrated curve corresponds to the measurement situation illustrated in FIG. 11.
Figure 15:
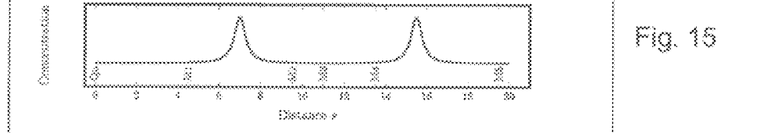
FIG. 15 shows the concentration of a gas, illustrated in a graph, with a local increase as a function of the distance from the radiation source Qu to the spectrometer S along the overall beam path. The illustrated curve corresponds to the measurement situation illustrated in FIG. 12.

The concentration $\rho_x(s)$ of the observed gas X with local inhomogeneity is sketched schematically in FIG. 14 and FIG. 15 for two different minor settings (corresponding to FIG. 11 and FIG. 12).

In the device sketched in FIG. 11/12, the mirror M3 is not mandatory and the light path can be guided directly from M2 to M4, wherein, however, the alignment of these two minors then needs to be suitably adapted. Analogously, the beam can be guided directly to the spectrometer S in the case of an appropriate orientation of the mirror M4. However, this variant requires simultaneous movement and rotation of all minors and moreover, as a result of the more complex geometry, more complicated modeling of the spectra during the evaluation, and so the advantage of a lower number of mirrors would only be relevant in the case of "poor" mirrors with r>>1.

As a result of the low background concentrations of the gases of interest, long path lengths are advantageous, and so optionally open multi-reflection cells are required. The configurations sketched in FIGS. 7 to 10 above can be appropriately extended in technically obvious fashion. In particular, in the design from FIGS. 11/12, which is advantageous due to the two-dimensional scanning, the light path can easily be doubled: if the last mirror M5 is aligned perpendicular to the beam direction, the incident beam ST is reflected back into the incidence direction and therefore passes over the whole beam path for a second time, cf. FIG. 17 in this respect.

Figure 16:
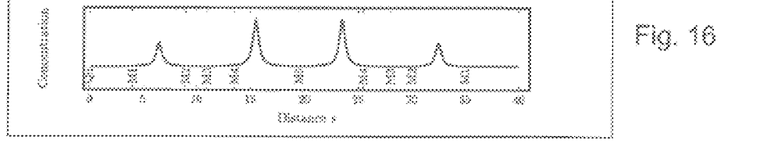
FIG. 16 shows the concentration of a gas, illustrated in a graph, with a local increase as a function of the distance from the radiation source Qu to the spectrometer S along the overall beam path. The illustrated curve corresponds to the measurement situation illustrated in FIG. 17.

The modeling of the optical depth in accordance with equation (10) should be modified here in an obvious fashion, i.e., the integral is substantially doubled with "mirrored" concentration $\bar{\rho}$:

$$\tau_X = \int_{Qu}^{S} k_X(\nu)\rho_X(s)\,ds + \int_{S}^{Qu} k_X(\nu)\bar{\rho}_X(s)\,ds$$

cf. FIG. 16. In typical cleanrooms with spatial dimensions of a few tens of meters, this then renders it possible to realize light path lengths of more than one hundred meters.

Figure 17:
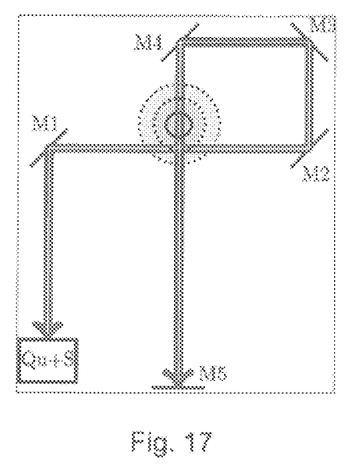
FIG. 17 shows a schematic diagram of a measurement geometry for two-dimensional scanning of the cleanroom. The mirror M5 is placed perpendicular to the incident beam ST, and so the beam ST is reflected and returned over the whole path via M4-M3-M2-M1.

In the measurement configurations sketched here, particularly in FIGS. 11, 12 and 17, it is impossible to avoid a widening of the beam ST as a result of the significant path lengths of a few tens to hundreds of meters. By using appropriate telescopes, as are used, for example, in atmospheric research for horizontal probing, it is possible to restrict the widening of the beam ST in the case of 100 m path length to approximately 10 cm. Alternatively and/or additionally, the widening of the light beam can be reduced by appropriately modified mirrors or retroreflectors.

When evaluating the measured spectra within the scope of a least squares fit according to equation (6), a discretization of the sought-after gas concentration(s) $\rho(\vec{r})=\rho(x, y)$ or $\rho(x, y, z)$ is required. Here, (x, y, z) denote the spatial coordinates; however, in the following text, only the two-dimensional case will be illustrated. Without loss of generality, the following text moreover only treats the case of one gas X to be determined and the subscript $\rho_X$ is omitted.

These embodiments render it possible to build up the state vector χ from the concentration ρ specified at M×N discrete nodes in space, i.e.:

χ=(ρ($x_1,y_1$),ρ($x_2,y_1$), ... ρ($x_M,y_1$),ρ($x_1,y_2$),
ρ($x_2,y_2$), ... , ... ρ($x_M,y_N$)).

However, in the case of a sufficiently good discretization, this leads to an ill-conditioned or ill-posed inverse problem, which cannot be solved in a sensible way without additional information (regularization).

Local contaminations in particular are of particular interest here, which contaminations can be caused by, e.g., leaks. In a first approximation, local increases in concentration can be modeled by bell-shaped distribution functions, i.e., by a Gaussian function:

ρ(x,y)=$\rho_b$+$\Delta_\rho$exp(-($x^2$+$y^2$)/$\delta^2$) (12)

or slightly more generally:

ρ(x,y)=$\rho_b$+$\Delta_\rho$exp[-(x/$\delta_x$)$^2$-(y/$\delta_y$)$^2$] (13)

where $\rho_b$ is the (spatially constant) background concentration, $\Delta_\rho$ is the amplitude of the concentration increase and δ, $\delta_x$, $\delta_y$ denote the typical (full width at half maximum) width of the increase, and the state vector χ of the least squares fit is formed by these three or four variables:

χ=($\rho_b$,$\Delta_\rho$,δ) or χ=($\rho_b$,$\Delta_\rho$,$\delta_x$,$\delta_y$). (14)

When modeling the transmission τ or the optical depth τ according to equation (10), the spatial coordinates x, y should be imaged on the path length variable s depending on the minor position.

Instead of evaluating the spectra recorded for various mirror positions individually, it is sensible to evaluate all spectra of a "measurement sequence" within the meaning of a "global fit." This is brought about by concatenating the measurement vectors (spectra) recorded for L different minor positions I=(P1, P2, ... ):

$$y_{obs}^1 \equiv T_{obs}^1, y_{obs}^2 \equiv T_{obs}^2, \ldots, y_{obs}^L \equiv T_{obs}^L,$$

to form an overall measurement vector:

$$Y_{obs} = (y_{obs}^1, y_{obs}^2, \ldots, y_{obs}^L) \tag{15}$$

in an analogous fashion to the vector of the model spectra $Y_{mod}$. The least squares problem from equation (6) then reads as:

$$\min_x \|Y_{obs} - Y_{mod}(x)\|^2 = \min_x \sum_{l=1}^L \|y_{obs}^l - y_{mod}^l(x)\|^2 = \\ \min_x \sum_{l=1}^L \sum_{i=1}^m \left[ \mathcal{T}_{obs}^l(\nu_i) - \mathcal{T}_{remainder}(\nu_i) \exp\left(-\int_{Path^l} k_X(\nu_i)\rho_X(s)\,ds\right) \right]^2 \tag{16}$$

As discussed above, the assumption is made here that the concentration of all other "remainder" gases is constant in the cleanroom and the transmission $\tau_{remainder}$ is therefore independent of the minor positions. Since all spectra of light paths that do not touch regions of increased concentration(s) are the same, these are irrelevant in this case and can be omitted, or it suffices to use only one of these "background spectra," or the noise-reduced spectrum from averaging all background spectra, in the evaluation.

As already explained above, the device according to the invention for establishing trace gas concentrations in an examination volume comprises a radiation source Qu, by means of which an electromagnetic beam can be generated, a beam guiding apparatus LE which is arranged downstream of the radiation source Qu and by means of which a multiplicity of variations of beam guidance of the beam entering the beam guiding apparatus LE can be set in an observation plane in the examination volume, a spectrometer S which is arranged downstream of the beam guiding apparatus LE and by means of which it is possible to carry out a spectral analysis of the beam leaving the beam guiding apparatus LE, a control unit SE for controlling the radiation source Qu, the beam guiding apparatus LE and the spectrometer S, and an evaluation unit AE, by means of which it is possible to establish in the observation plane a 2D concentration distribution for one or more trace gases in the examination volume on the basis of the spectral analysis for the different variations of beam guidance. Thus, the beam guidance takes place in a two-dimensional observation plane, and so the gas concentrations that can be established hereby specify a two-dimensional concentration distribution, for example, in (x, y)-coordinates.

By way of example, the beam guidance of the beam guiding apparatus LE can have one of the above-described embodiments, cf., in particular, FIGS. 7-13 and 17 in this respect. In any case, the beam guiding apparatus LE serves to bring about different variations of beam guidance and thus, as it were, "scan" the observation plane by means of different instances of beam guidance. The two-dimensional resolution of the 2D concentration distribution established thereby depends on the scanning density, i.e., on the variations of beam guidance in the observation plane.

The beam source Qu is preferably a beam source emitting infrared light (FIR, MIR, NIR) and/or microwave radiation and/or visible light and/or UV light. The spectrometer S is preferably a differential optical absorption spectrometer (DOAS) or a Fourier transform infrared spectrometer (FTIR).

A particularly preferred development of the device according to the invention is distinguished by virtue of the fact that the beam guiding unit LE comprises two first beam deflection units M1 and M2, which are spaced apart from one another by a distance A1 and between which a first beam axis, which lies in the observation plane, is formed, two second beam deflection units M4 and M5, which are spaced apart from one another by a distance A2 and between which a second beam axis, which lies in the observation plane and extends orthogonally to the first beam axis, is formed, and a third beam deflection unit M3, wherein, in order to set the beam guidance, the first beam deflection units M1 and M2 can be displaced together in the observation plane, orthogonally with respect to the first beam axis, and the second beam deflection units M4 and M5 can be displaced together in the observation plane, orthogonally with respect to the second beam axis, wherein the first and the second beam axis always cross between the beam deflection units M1 and M2 and between the beam deflection units M4 and M5; the beam deflection unit M3 is fixedly arranged in the observation plane and the beam guiding unit LE is designed and conFigured in such a way that a beam emitted by the beam source Qu is always directed to the spectrometer S via a first overall beam path: Qu-M1-M2-M3-M4-M5-S or via a second overall beam path: Qu-M1-M2-M3-M4-M5-M4-M3-M2-M1-S.

As a result of a continuous or incremental displacement of the beam deflection units M1/M2 or M4/M5, these embodiments render possible an effective scanning of the observation plane and hence an effective capture/establishment of the 2D concentration distribution in the observation plane, which is preferably a horizontal plane. The distances A1 and A2 are preferably constant in each case but can also be varied individually, depending on application. The beam deflection units M1-M5 are preferably mirrors, which are adjusted in such a way that the first or the second overall beam path can be realized in each case.

A further particularly preferred development of the device according to the invention is distinguished by virtue of the fact that an actuatable mechanism is present, by means of which at least the beam guiding apparatus LE is displaceable orthogonally with respect to the observation plane, wherein every position of the beam guiding apparatus LE generatable thereby uniquely defines an associated observation plane, the mechanism, for the actuation thereof, is connected to the control unit SE, and the evaluation unit AE is designed and configured in such a way that a 3D concentration distribution for the one or more trace gases can be established on the basis of the 2D concentration distributions established for different observation planes.

The examination volume is preferably a cleanroom with a rectangular floor plan, wherein the distance A1 substantially equals the width of the floor plan and the distance A2 substantially equals the length of the floor plan, or vice versa. It is furthermore preferable for the beam source Qu and the spectrometer S to be combined in one unit, wherein, for the first overall beam path: Qu-M1-M2-M3-M4-M5-S, an emission direction of the beam leaving the unit in the direction of the beam deflection unit M1 differs by 90° from an arrival direction of the beam incident on the spectrometer S from the beam deflection unit M5.

The device according to the invention renders possible the simultaneous detection of (trace) gases in closed rooms such as, in particular, laboratories or cleanrooms, and the quantitative determination of the concentrations thereof with a high temporal and spatial resolution without interaction between the various gases and without adversely affecting/falsifying the volume of air to be examined. As a result of the preferred short measurement times (seconds to at most minutes) the measurements can be carried out at regular intervals and in an automated fashion. The preferred use of compact absorption or multi-reflection cells in the beam path allows a spatially highly resolved capture of even low gas concentrations; in the case of superposition of the absorption signatures of the gases of interest with further interfering gases, identification is improved in the case of reduced pressure in the closed absorption cell. As a result of the low computational requirements in respect of the evaluation algorithm, the results (concentrations) are available immediately.

Further advantages, features and details emerge from the following description, in which—optionally with reference to the drawing—at least one exemplary embodiment is described in detail. Described and/or depicted features form the subject matter of the invention, on their own or in any sensible combination, optionally also independently of the claims, and can in particular additionally also be the subject matter of one or more separate applications. The same, similar and/or functionally equivalent parts are provided with the same reference signs.

Figure 18:
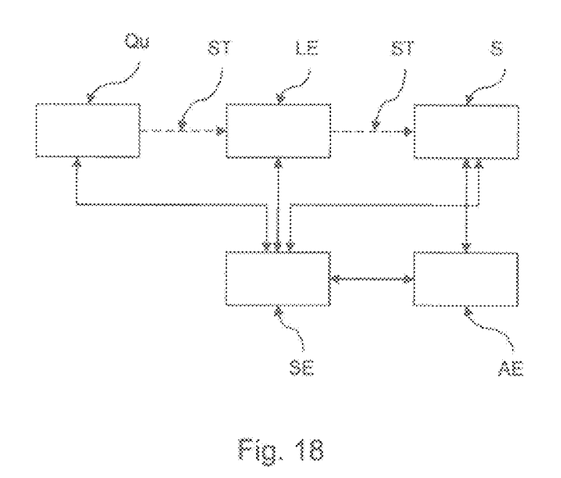
FIG. 18 shows a schematic design of a device according to the invention.

FIG. 18 shows a schematic design of a device according to the invention for establishing gas concentrations in an examination volume Vol, comprising a radiation source Qu, by means of which an electromagnetic beam ST can be generated, a beam guiding apparatus LE which is arranged downstream of the radiation source Qu and by means of which a multiplicity of variations of beam guidance of the beam ST entering the beam guiding apparatus LE can be set in an observation plane in the examination volume, a spectrometer S which is arranged downstream of the beam guiding apparatus LE and by means of which it is possible to carry out a spectral analysis of the beam ST leaving the beam guiding apparatus LE, a control unit SE for controlling the radiation source Qu, the beam guiding apparatus LE and the spectrometer S, and an evaluation unit AE, by means of which it is possible to establish in the observation plane a 2D concentration distribution for one or more gases in the examination volume Vol on the basis of the spectral analysis for the different variations of beam guidance.

Figure 19:
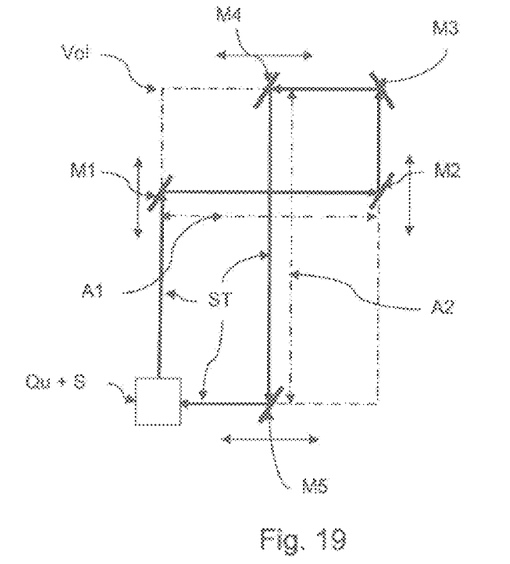
FIG. 19 shows a preferred embodiment of the beam guiding unit LE.

FIG. 19 shows a preferred embodiment of the beam guiding unit LE which is distinguished by virtue of the fact that the beam guiding unit LE comprises two first beam deflection units M1 and M2, which are spaced apart from one another by a distance A1 and between which a first beam axis, which lies in the observation plane, is formed, two second beam deflection units M4 and M5, which are spaced apart from one another by a distance A2 and between which a second beam axis, which lies in the observation plane and extends orthogonally to the first beam axis, is formed, a beam deflection unit M3, wherein, in order to set the beam guidance, the first beam deflection units M1 and M2 can be displaced together in the observation plane, orthogonally with respect to the first beam axis, and the second beam deflection units M4 and M5 can be displaced together in the observation plane, orthogonally with respect to the second beam axis, wherein the first and the second beam axis always cross between the beam deflection units M1 and M2 and between the beam deflection units M4 and M5; the beam deflection unit M3 is fixedly arranged in the observation plane and the beam guiding unit LE is designed and configured in such a way that a beam ST emitted by the beam source Qu is always directed to the spectrometer S via a first overall beam path: Qu-M1-M2-M3-M4-M5-S or via a second overall beam path: Qu-M1-M2-M3-M4-M5-M4-M3-M2-M1-S. The arrows indicate the displaceability of the beam deflection units M1/M2 and M4/M5.

What is claimed is:

1. A device for establishing gas concentrations in an examination volume, the device comprising:
   a radiation source configured to generate an electromagnetic beam;
   a beam guiding apparatus arranged downstream of the radiation source, the beam guiding apparatus configured to set a plurality of variations of beam guidance of the beam entering the beam guiding apparatus in an observation plane in the examination volume, wherein the beam guiding apparatus comprises:
      two first beam deflection devices that are spaced apart from one another by a distance A1 on a first beam axis, and
      two second beam deflection devices that are spaced apart from one another by another distance A2 on a second beam axis, wherein the observation plane includes portions of the first beam axis and the second beam axis; and
   a spectrometer arranged downstream of the beam guiding apparatus, the spectrometer configured to carry out a spectral analysis of the beam leaving the beam guiding apparatus;
   wherein an output of the spectrometer is configured to be used as a basis to establish in the observation plane a 2D concentration distribution for one or more gases in the examination volume on the basis of the spectral analysis for different variations of beam guidance.

2. The device as claimed in claim 1, wherein the second beam axis is orthogonal to the first beam axis.

3. The device as claimed in claim 2, wherein the examination volume is a cleanroom with a rectangular floor plan with a length and a width, wherein the distance A1 substantially equals the width and the distance A2 substantially equals the length of the floor plan, or vice versa.

4. The device as claimed in claim 2, wherein, in order to set the beam guidance, the first beam deflection devices are configured to be displaced together in the observation plane, orthogonally with respect to the first beam axis, and the second beam deflection devices are configured to be displaced together in the observation plane, orthogonally with respect to the second beam axis, wherein the first and the second beam axis always cross between the beam deflection devices and between the beam deflection devices.

5. The device as claimed in claim 4, wherein the beam guiding apparatus is configured in such a way that a beam emitted by the radiation source is always directed to the spectrometer via a first overall beam path: Qu-M1-M2-M4-M5-S or via a second overall beam path: Qu-M1-M2-M4-M5-M4-M2-M1-S, where Qu is the radiation source, M1 and M2 are the first beam deflection devices, M4 and M5 are the second beam deflection devices and S is the spectrometer.

6. The device as claimed in claim 5, wherein the beam guiding apparatus is configured in such a way that a beam emitted by the radiation source is always directed to the spectrometer via the first overall beam path.

7. The device as claimed in claim 5, wherein the radiation source and the spectrometer are combined in one device and wherein, for the first overall beam path, an emission direction of the beam leaving the device in the direction of the first beam deflection device M1 differs by 90° from an arrival direction of a beam incident on the spectrometer S from the second beam deflection unit M5.

8. The device as claimed in claim 5, wherein the first and second beam deflection devices M1, M2, M4, M5 comprise mirrors.

9. The device as claimed in claim 5, wherein the beam guiding apparatus is configured in such a way that a beam emitted by the radiation source is always directed to the spectrometer via the second overall beam path.

10. The device as claimed in claim 1,
wherein, in order to set the beam guidance, the first beam deflection devices are configured to be displaced together in the observation plane, orthogonally with respect to the first beam axis, and the second beam deflection devices are configured to be displaced together in the observation plane, orthogonally with respect to the second beam axis, wherein the first and the second beam axis always cross between the first beam deflection devices and between the second beam deflection devices; and
wherein the beam guiding apparatus is configured in such a way that a beam emitted by the radiation source is always directed to the spectrometer via a first overall beam path: Qu-M1-M2-M4-M5-S or via a second overall beam path: Qu-M1-M2-M4-M5-M4-M2-M1-S, where Qu is the radiation source, M1 and M2 are the first beam deflection devices, M4 and M5 are the second beam deflection devices and S is the spectrometer.

11. The device as claimed in claim 10, wherein the beam guiding apparatus has a further beam deflection device fixedly arranged in the observation plane and wherein the beam guiding apparatus is configured in such a way that a beam emitted by the radiation source is always directed to the spectrometer via a first overall beam path: Qu-M1-M2-M3-M4-M5-S or via a second overall beam path: Qu-M1-M2-M3-M4-M5-M4-M3-M2-M1-S, where M3 is the further beam deflection device.

12. The device as claimed in claim 1, further comprising:
a controller configured to control the radiation source, the beam guiding apparatus, and the spectrometer; and
an actuatable mechanism configured to displace the beam guiding apparatus orthogonally with respect to the observation plane, wherein every position of the beam guiding apparatus uniquely defines an associated observation plane, the actuatable mechanism being connected to the controller.

13. The device as claimed in claim 12, wherein a 3D concentration distribution for the one or more gases is configured to be established on the basis of the 2D concentration distributions established for different observation planes.

14. The device as claimed in claim 1, wherein the observation plane is a horizontal plane.

15. The device as claimed in claim 1, wherein the radiation source and the spectrometer are combined in one device.

16. The device as claimed in claim 1, wherein the radiation source comprises a beam source emitting infrared light and/or microwave radiation and/or visible light and/or UV light.

17. The device as claimed in claim 1, wherein the spectrometer comprises a differential optical absorption spectrometer.

18. The device as claimed in claim 1, wherein the spectrometer comprises a Fourier transform infrared spectrometer.

19. The device as claimed in claim 1, further comprising a controller configured to control the radiation source, the beam guiding apparatus, and the spectrometer.

20. A device for establishing gas concentrations in an examination volume, the device comprising:
a radiation source configured to generate an electromagnetic beam;
a beam guiding apparatus arranged downstream of the radiation source, the beam guiding apparatus configured to sequentially set a plurality of variations of beam guidance of the beam entering the beam guiding apparatus such that a plurality of observation areas in the examination volume are sequentially set by the beam guiding apparatus, wherein the beam guiding apparatus comprises two first beam deflection devices that are spaced apart from one another by a first distance, wherein the two first beam deflection devices are configured to be moved synchronously along a first direction;
a spectrometer arranged downstream of the beam guiding apparatus, the spectrometer configured to carry out a spectral analysis of the beam leaving the beam guiding apparatus for each of the plurality of observation areas; and
wherein the device is configured to establish a multi-dimensional distribution of a concentration for one or more gases in the examination volume based on the spectral analysis for each of the plurality of observation areas.

21. The device as claimed in claim 20, wherein the beam guiding apparatus is configured to direct the beam along a first axis and a orthogonal second axis, wherein the first axis and the second axis form an observation area of the plurality of observation areas.

22. The device as claimed in claim 21, wherein, based on each of the spectral analysis of the beam, a two dimensional distribution of the concentration for one or more gases in the observation area is configured to be established.

23. The device as claimed in claim 20, wherein the beam guiding apparatus comprises:
two second beam deflection devices that are spaced apart from one another by a second distance, wherein the two second beam deflection devices are configured to be moved synchronously along a second direction orthogonal to the first direction.

24. The device as claimed in claim 20, wherein a path length of the beam is identical for all positions set by the beam guiding apparatus.

25. A method for establishing gas concentrations in an examination volume, the method comprising:
generating an electromagnetic beam using a radiation source;
providing a beam guiding apparatus downstream of the radiation source, wherein the beam guiding apparatus comprises a plurality of mirrors;
sequentially setting a plurality of variations of beam guidance of the beam entering the beam guiding apparatus such that a plurality of observation areas in the examination volume are sequentially set by the beam guiding apparatus, wherein, for each setting, two first mirrors of the plurality of mirrors are spaced apart from one another by a first distance on a first beam axis, and wherein two second minors of the plurality of mirrors are spaced apart from one another by a second distance on a second beam axis;
providing a spectrometer arranged downstream of the beam guiding apparatus;
performing a spectral analysis of the beam leaving the beam guiding apparatus for each of the plurality of observation areas; and
establishing a multi-dimensional distribution of a concentration for one or more gases in the examination volume using the spectral analysis for each of the plurality of observation areas.

26. A device for establishing gas concentrations in an examination volume, the device comprising:

a radiation source configured to generate an electromagnetic beam;

a beam guiding apparatus arranged downstream of the radiation source, the beam guiding apparatus configured to set a plurality of variations of beam guidance of the beam entering the beam guiding apparatus in an observation plane in the examination volume; and a spectrometer arranged downstream of the beam guiding apparatus, the spectrometer configured to carry out a spectral analysis of the beam leaving the beam guiding apparatus, wherein the beam guiding apparatus comprises a plurality of beam deflection devices fixedly arranged in the observation plane, and the beam guiding apparatus is configured in such a way that a beam emitted by the radiation source is directed to the spectrometer through two different overall beam paths, and wherein an output of the spectrometer is configured to be used as a basis to establish in the observation plane a 2D concentration distribution for one or more gases in the examination volume on the basis of the spectral analysis for different variations of beam guidance.

27. The device as claimed in claim 26, wherein the beam guiding apparatus is configured in such a way that a beam emitted by the radiation source is always directed to the spectrometer via a first overall beam path: Qu-M1-M2-M3-M4-M5-S or via a second overall beam path: Qu-M1-M2-M3-M4-M5-M4-M3-M2-M1-S, where Qu is the radiation source, S is the spectrometer, and M1, M2, M3, M4 and M5 are the plurality of beam deflection devices.

28. The device as claimed in claim 27, wherein the first and second beam deflection devices M1, M2, M4, M5 comprise mirrors, and beam deflection device M3 comprises a minor.

* * * * *

UNITED STATES PATENT AND TRADEMARK OFFICE
CERTIFICATE OF CORRECTION

| | | |
|---|---|---|
| PATENT NO. | : 9,201,007 B2 | Page 1 of 1 |
| APPLICATION NO. | : 13/851879 | |
| DATED | : December 1, 2015 | |
| INVENTOR(S) | : Dieter Kohlert et al. | |

It is certified that error appears in the above-identified patent and that said Letters Patent is hereby corrected as shown below:

In the claims

In Col. 16, line 54, claim 25, delete "two second minors" and insert --two second mirrors--.

Signed and Sealed this
Twelfth Day of April, 2016

Michelle K. Lee
*Director of the United States Patent and Trademark Office*